United States Patent
Schneider et al.

(10) Patent No.: US 8,091,407 B2
(45) Date of Patent: Jan. 10, 2012

(54) METHOD AND DEVICE FOR MONITORING A FLOW OF LIQUID FOR THE PRESENCE OF AIR BY MEANS OF ULTRASOUND

(75) Inventors: Jochen Schneider, Wipfeld (DE); Ralf Wamsiedler, Gochsheim-Weyer (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 563 days.

(21) Appl. No.: 11/921,629

(22) PCT Filed: May 31, 2006

(86) PCT No.: PCT/EP2006/005171
§ 371 (c)(1),
(2), (4) Date: May 21, 2008

(87) PCT Pub. No.: WO2006/128683
PCT Pub. Date: Dec. 7, 2006

(65) Prior Publication Data
US 2008/0282804 A1    Nov. 20, 2008

(30) Foreign Application Priority Data
Jun. 3, 2005  (DE) .......................... 10 2005 025 500

(51) Int. Cl.
*G01N 29/00* (2006.01)
*A61M 31/00* (2006.01)
(52) U.S. Cl. ...................................... 73/19.03; 604/67
(58) Field of Classification Search ................. 73/19.03; 604/65, 67
See application file for complete search history.

(56) References Cited

U.S. PATENT DOCUMENTS

| 4,487,601 A | | 12/1984 | Lindemann |
| 4,607,520 A | * | 8/1986 | Dam ............................ 73/19.03 |
| 4,651,555 A | | 3/1987 | Dam |
| 4,981,467 A | * | 1/1991 | Bobo et al. ...................... 604/65 |

(Continued)

FOREIGN PATENT DOCUMENTS

| EP | 1182452 | 2/2002 |
| EP | 1466637 | 10/2004 |

OTHER PUBLICATIONS

International Search Report for PCT/EP2006/005171.

(Continued)

*Primary Examiner* — Hezron E Williams
*Assistant Examiner* — Nathaniel Kolb
(74) *Attorney, Agent, or Firm* — Kenyon & Kenyon LLP

(57) ABSTRACT

The invention relates to a method and a device for monitoring a flow of liquid for the presence of air bubbles, in particular the blood flowing in an extracorporeal blood circuit of an extracorporeal blood treatment device. The air bubbles are detected by an ultrasound measurement and the ultrasound signals received in a continuous sequence of time intervals are each compared to a predetermined reference level. When the amplitude of the ultrasound signal, or a parameter correlating to the amplitude of the ultrasound signal, is less than the predetermined reference level, the presence of a defined volume of air is determined. When the number of times the ultrasound signal is less that the predetermined reference value if is greater than the set limit value, it is determined that a critical volume of air is present in the patient's blood and the dialysis is stopped.

9 Claims, 3 Drawing Sheets

U.S. PATENT DOCUMENTS

| | | | | |
|---|---|---|---|---|
| 5,176,631 A | * | 1/1993 | Koenig | 604/65 |
| 5,394,732 A | * | 3/1995 | Johnson et al. | 73/19.1 |
| 5,824,881 A | | 10/1998 | Shouldice et al. | |
| 2005/0124929 A1 | * | 6/2005 | Katz et al. | 604/65 |
| 2005/0192529 A1 | * | 9/2005 | Butterfield et al. | 604/65 |

OTHER PUBLICATIONS

English translation of the International Preliminary Report on Patentability for PCT/EP2006/005171.

* cited by examiner

Air event for which n = 5

| BP-Rate [ml/min] | N | BP-Rate [ml/min] | N | BP-Rate [ml/min] | N | BP-Rate [ml/min] | N | BP-Rate [ml/min] | N |
|---|---|---|---|---|---|---|---|---|---|
| 100 | 192 | 200 | 108 | 300 | 68 | 400 | 56 | 500 | 48 |
| 110 | 184 | 210 | 104 | 310 | 68 | 410 | 56 | 510 | 48 |
| 120 | 172 | 220 | 100 | 320 | 68 | 420 | 56 | 520 | 48 |
| 130 | 160 | 230 | 92 | 330 | 64 | 430 | 56 | 530 | 48 |
| 140 | 152 | 240 | 88 | 340 | 64 | 440 | 56 | 540 | 44 |
| 150 | 144 | 250 | 84 | 350 | 64 | 450 | 52 | 550 | 44 |
| 160 | 136 | 260 | 80 | 360 | 60 | 460 | 52 | 560 | 44 |
| 170 | 128 | 270 | 76 | 370 | 60 | 470 | 52 | 570 | 44 |
| 180 | 120 | 280 | 72 | 380 | 60 | 480 | 52 | 580 | 44 |
| 190 | 112 | 290 | 72 | 390 | 60 | 490 | 48 | 590 | 44 |
|  |  |  |  |  |  |  |  | 600 | 44 |

METHOD AND DEVICE FOR MONITORING A FLOW OF LIQUID FOR THE PRESENCE OF AIR BY MEANS OF ULTRASOUND

FIELD OF THE INVENTION

The present invention relates to a method of monitoring a flowing liquid, and in particular the blood flowing in an extra-corporeal blood circulatory system of an extra-corporeal blood treating apparatus, for the presence of air, and to a method for the extra-corporeal treatment of blood using an extra-corporeal blood circulatory system, in which the presence of air in the extra-corporeal blood circulatory system is monitored for. The present invention also relates to an arrangement for monitoring a flowing liquid, and in particular the blood flowing in an extra-corporeal blood circulatory system, for the presence of air, and to an apparatus for the extra-corporeal treatment of blood having an arrangement for monitoring the blood flowing in the extra-corporeal blood circulatory system of the blood treating apparatus for the presence of air.

BACKGROUND OF THE INVENTION

Various methods are known for the extra-corporeal treatment of blood in which the patient's blood flows through a blood treating unit in an extra-corporeal blood circulatory system. One of the chief complications of the extra-corporeal treatment of blood, such for example as hemodialysis or hemofiltration, is the possibility of air penetrating into the extra-corporeal blood circulatory system.

To separate entrained air bubbles from the blood, drip chambers are arranged in the venous segment of the extra-corporeal blood circulatory system. The known drip chambers are highly reliable in trapping the air bubbles. Nevertheless, there is a risk of air bubbles being infused into the patient intravenously. For further safety, parts of the blood treating apparatus have air detectors, for whose reliability in operation very stringent requirements are set. Air detectors must be capable of detecting large and small air bubbles with high reliability. If a large air bubble is detected, the treatment is immediately suspended and an alarm given, although a certain number of smaller air bubbles can be tolerated. However, the total volume of air contained in the blood must not exceed a preset limiting value.

EP 1182452 A2 describes an arrangement for detecting air bubbles in flowing liquids that is based on ultrasonic measurement. The air bubbles are detected from the attenuation of ultrasonic signals traveling through a measurement gap. The amount of attenuation is a measure of the size of the air bubbles.

The monitoring arrangement disclosed in EP 1182452 has an ultrasonic emitter for coupling the ultrasonic signals into the flowing liquid at a preset level and an ultrasonic receiver for receiving the ultrasonic signals emerging from the flowing liquid. The output signal from the ultrasonic receiver is compared with a preset limiting value. If the ultrasonic signal is below the limiting value it is assumed that there is a large air bubble present. If the ultrasonic signal is equal to or above the limiting value it is assumed that there is a small air bubble present.

When there is a large air bubble, the monitoring arrangement at once gives an alarm. The occurrence of smaller air bubbles, on the other hand, does not immediately result in an alarm. An alarm is only given when the air situated in the flowing liquid exceeds a critical total volume. The volume of air contained in the liquid is calculated from the number of small air bubbles and the flow-rate of the flowing liquid. The small air bubbles that are detected by the ultrasonic measurement are counted for this purpose. The monitoring arrangement known from EP 1182452 A2 is intended particularly for monitoring the extra-corporeal blood circulatory system of a blood treating apparatus.

U.S. Pat. No. 4,651,555 describes a method of monitoring a flowing liquid for the presence of particles or gas bubbles, in which sound signals are coupled into the flow of liquid and the sound signals emerging from the liquid are received. The sound signals received are compared with a limiting value, and it is concluded that an air bubble is present if the sound signals received are lower than the limiting value. The limiting value with which the sound signals are compared is determined on the basis of a mean value which is formed from the sound signals received.

A monitoring method for flowing fluids which is based on the analysis of the damping of sound signals which travel across a measuring gap is also known from U.S. Pat. No. 4,487,601.

EP 1466637 A2 describes an arrangement for detecting air bubbles on the basis of an ultrasonic measurement, in which the envelope of the signal received is analyzed to allow the volume of the air bubbles to be determined. If the total volume of the air bubbles exceeds a preset limiting value within a given period of time, an alarm is triggered.

SUMMARY OF THE INVENTION

One aspect of the present invention is to specify a method of monitoring a flowing liquid for the presence of air, which allows a distinction to be made with high reliability between large and small air bubbles, and allows different incidents to be detected.

A further aspect of the present invention is to specify a method for the extra-corporeal treatment of blood using an extra-corporeal blood circulatory system, in which method, with high reliability, large and small air bubbles can be detected in the extra-corporeal circulatory system and a distinction can be made between different incidents.

Another aspect of the invention is also to provide a system for monitoring a flowing liquid for the presence of air and an extra-corporeal apparatus for the treatment of blood for use with this system.

The present invention can distinguish between large and small air bubbles by the attenuation of a single ultrasonic pulse being used and by the amplitude of each of the ultrasonic signals that are received in a continuous sequence of intervals of time being compared with a preset reference level, that number of successive intervals of time being determined in which the amplitude of the ultrasonic signal received in the given interval of time is below the preset reference level. The determined number of successive intervals of time in which the amplitude of the ultrasonic signal received is below the preset reference level is compared in turn with a limiting value that is laid down as a function of the flow-rate of the flowing liquid. It is determined that there is an incident when the number of successive intervals of time is above the limiting value laid down. When this is the case, it is assumed that a large air bubble is present.

The limiting value that is compared with the number of successive intervals of time can be determined empirically in trials, taking into account various safety criteria. As the flow-rate of the flowing liquid rises, the limiting value becomes smaller. Hence it is only concluded that there is an incident when a given volume of air is detected in a given number of successive intervals of time. Consequently, there is not assumed to be an incident when, even though the number of intervals of time in which a given volume of air is detected exceeds the critical limiting value, the intervals of time do not succeed one another continuously. Hence, it is not simply the total number of events that is important.

In the event of the number of successive intervals of time in which a given volume of air is detected being equal to or below the limiting value laid down, it is determined that what is contained in the liquid is not one large air bubble or a large volume of air, but rather only one or more small air bubbles or a small volume of air (individual bubbles). This small volume of air can be tolerated as long as it does not exceed a critical size.

In one embodiment, instead of the amplitude of the ultrasonic signal, any parameter which correlates with amplitude can be used for comparison. In this way, the maximum amplitude of the signal or only the amplitude of the upper or lower half-wave, for example, maybe analyzed. With signals in pulse form, for example, whose amplitude declines with time, it is preferably the maximum signal amplitude that is determined. In this case the amplitude is always a positive value, even if the absolute value of the signal were to be negative at a given point in time.

In another embodiment of the present invention, the number of events in which a small volume of air is detected is determined, and the number of such events is compared with a preset reference value. It is determined that there is an incident if the number of events exceeds the preset reference value, which means the total volume of air contained in the liquid has exceeded the critical amount. When an incident is detected, a first alarm signal and/or control signal is preferably generated. In an extra-corporeal apparatus for treating blood, an alarm is given and/or the treatment is suspended when an alarm signal and/or control signal is generated. The alarm mechanism can be of the type known in the prior art.

In another embodiment of the invention, different signals are generated when the amplitude of the ultrasonic signal received is below, equal to, or above the preset reference level, and the temporal sequence of the different signals is stored. Thus, a nuanced statement can be made regarding the size of the air bubbles present in the flowing liquid and their distribution.

The amplitude of the ultrasonic signal received can be compared with only one preset reference level to enable a distinction to be made between a larger and a smaller volume of air. It is also possible for a plurality of preset reference levels to be defined to enable air bubbles of different volumes to be differentiated from one another.

It is particularly advantageous if the two signals that are generated when the limiting value is exceeded or when the limiting value is not reached, respectively, are pulse width modulated (PWM) signals of different pulse widths. PWM signals can be transmitted with a high degree of immunity from interference because a pulse width modulated signal can be clearly distinguished from a spurious signal. In this way, a break in a line, which results in a signal not being received, can be reliably detected as well.

The length of the intervals of time at which the ultrasonic signals are analyzed, i.e. the sampling frequency, should be sized in such a way that adequate temporal resolution is possible. The sampling frequency is preferably about 5 kHz (T=200 μs). Because, at T=50 ms, the machine cycle of the known parts of blood treating apparatus is appreciably longer than the temporal spacing of the measuring cycles, the first and second signals, which are preferably PWM signals, are combined into signal blocks and the signal blocks are buffer stored prior to analysis. After the buffer storage, the signal blocks can be analyzed with the same timing as applies to the apparatus.

The components required for the analysis of the signal are generally present in known parts of blood treating apparatus. They include for example a computer by which, once suitably programmed, the requisite comparisons and calculations can be performed.

BRIEF DESCRIPTION OF THE DRAWINGS

An embodiment of the invention will be explained in detail below by reference to the drawings.

DETAILED DESCRIPTION OF THE DRAWINGS

Figure 1:
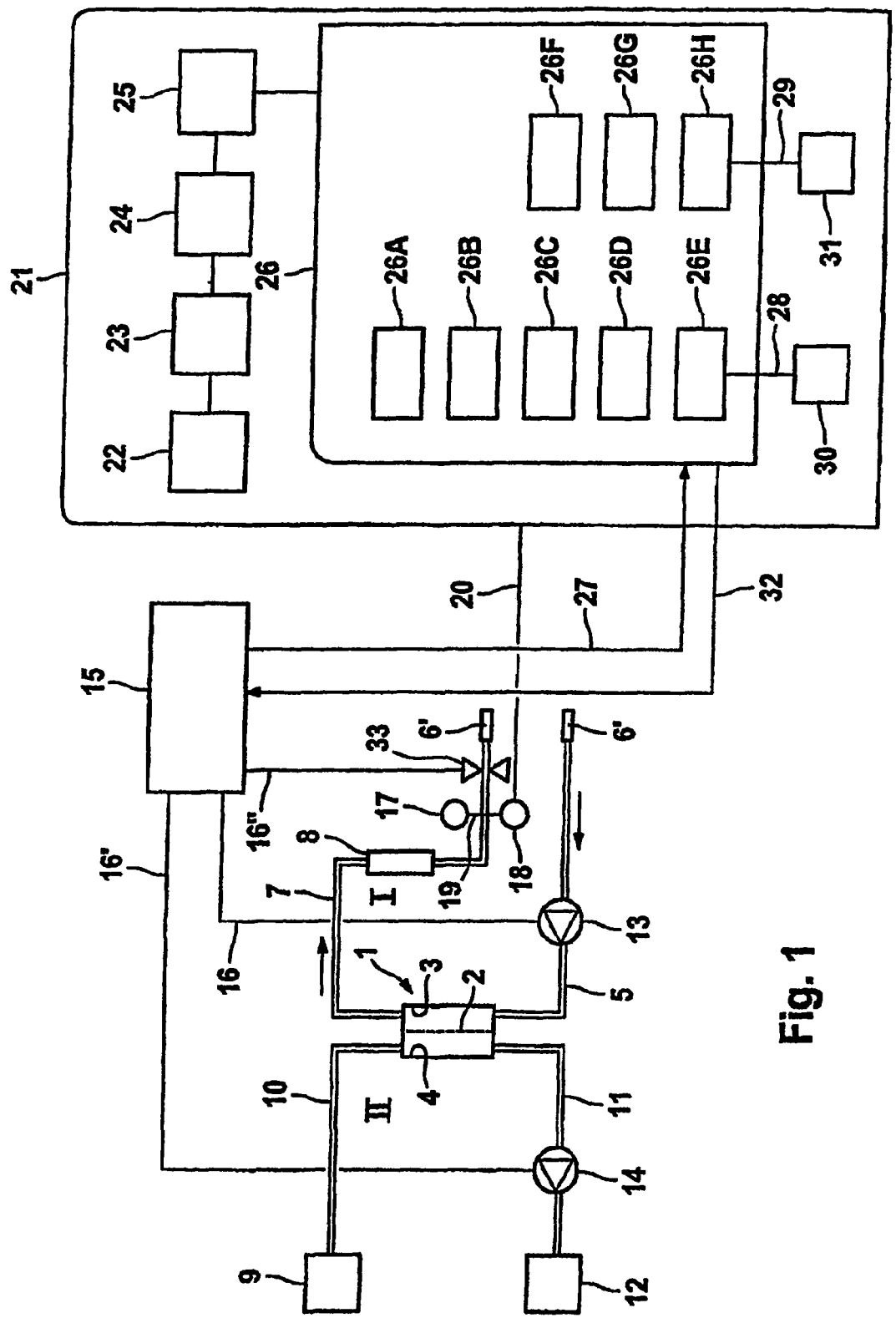
FIG. 1 is a simplified schematic representation of the principal components of a blood treatment apparatus having an extra-corporeal blood circulatory system, together with an arrangement for monitoring the blood flowing in the blood circulatory system for the presence of air bubbles.

FIG. 1 shows the principal components of the blood treating apparatus, together with the monitoring arrangement. The blood treating apparatus, such as a hemodialysis apparatus for example, has a dialyzer 1 which is divided by a semi-permeable membrane 2 into a blood chamber 3 and a dialysis liquid chamber 4. The inlet to the blood chamber 3 is connected to one end of a blood supply line 5, while the outlet from the blood chamber 3 is connected to one end of a blood takeaway line 7, into which a drip chamber 8 is connected. The other ends of the blood supply and takeaway lines 5, 7 are connected to arterial and venous needles 6 and 6' respectively. Arranged between the drip chamber 8 and the venous needle 6' is an electromagnetically actuatable venous tube clamp 33 for clamping off the blood takeaway line 7. Together with the blood chamber 3 of the dialyzer 1, the blood supply and takeaway lines 5, 7 constitute the extra-corporeal blood circulatory system I of the hemodialysis apparatus.

The dialysis liquid system II of the hemodialysis apparatus comprises a means 9 for processing the dialysis liquid, from which runs a dialysis liquid supply line 10 which goes to the dialysis liquid chamber 4 of the dialyzer 1. A dialysis liquid takeaway line 11, which goes to an outlet 12, runs from the dialysis liquid chamber 4. Arranged in the blood supply line 5 is a blood pump 13, while in the dialysis liquid takeaway line 11 there is arranged a dialysis liquid pump 14. During the treatment of the blood, the blood pump 13 and dialysis liquid pump 14 pump blood through the extra-corporeal blood circulatory system I and dialysis liquid through the dialysis liquid system II, respectively.

The hemodialysis apparatus comprises a central control unit 15 which is connected via control lines 16, 16' and 16" to the blood pump 13, the dialysis liquid pump 14 and the tube clamp 33, respectively. The hemodialysis apparatus also has a device for monitoring the blood flowing in the extra-corporeal blood circulatory system I for the presence of air bubbles.

In the case of the embodiment described, this monitoring device is part of the hemodialysis apparatus, but it may alternatively be a separate sub-assembly.

The monitoring device has an ultrasonic emitter 17 and an ultrasonic receiver 18. The emitter 17 and receiver 18 are arranged opposite one another on the measurement gap 19, on the opposite sides of the blood takeaway line 7, downstream of the drip chamber 8. The ultrasonic emitter 17 generates ultrasonic signals continuously in the pulsed mode at given intervals of time, for example T=200 µs (F=5 kHz). The ultrasonic signals, which have a preset maximum amplitude, travel across the measurement gap 19 and are received by the ultrasonic receiver 18. The receiver 18 generates electrical output signals which are proportional to the amplitude of the ultrasonic signals received. The output signals from the receiver 18 are fed via a signal line 20 to the analyzing unit 21.

The analyzing unit 21 has a circuit 22 for signal processing, a comparator 23, a circuit 24 for pulse width modulation (PWM), a buffer store 25 and a circuit 26 for signal analysis. The individual components may be of analog or digital design. The components are part of the hardware or software of the blood treatment apparatus.

The continuous sequence of output signals from the ultrasonic receiver 18 is fed to the circuit 22, in which the signals are processed for further analysis. The processed signals are then fed to the comparator 23, which compares the maximum amplitude of each signal with a preset reference level. In one embodiment, the amplitude, or a parameter which correlates therewith, is a measure of the attenuation of the signal that depends on the volume of air contained in the blood. Because the signals are pulsed ones, whose amplitude declines with time, the maximum amplitude of the signal is determined as the signal level to be analyzed. The preset reference level is a value that is characteristic of a relatively small given volume of air.

The comparator 23 compares each of the signals that are received in the continuous sequence of intervals of time with the preset reference level. If the maximum amplitude of the signal is below the preset level, it is determined that the given volume of air is present in the blood. Otherwise it is determined that the given volume of air is not present in the blood.

Figure 2:
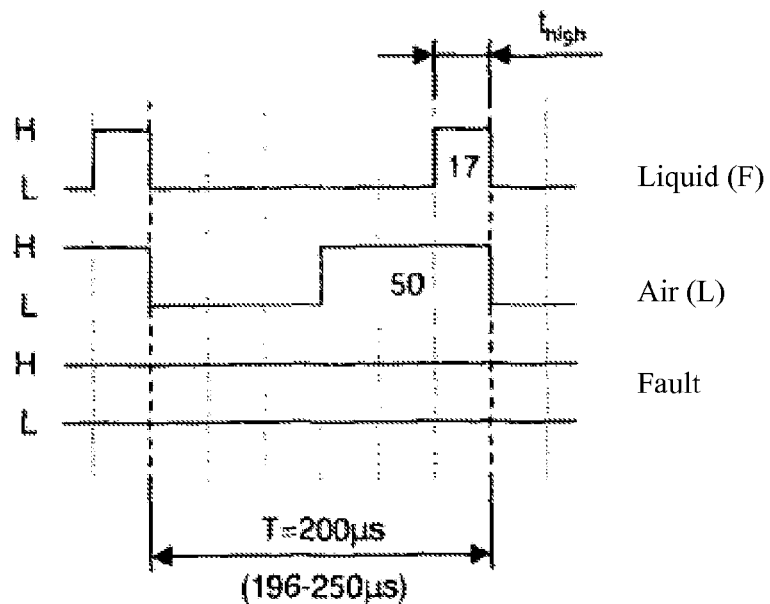
FIG. 2 shows the pulse width modulated signals for liquid and air.

The output signal from the comparator 23 is fed to the circuit 24 for pulse width modulation. The circuit 24 for pulse width modulation generates two pulse width modulated signals (PWM signals) as a function of the output signal from the circuit 24. If the maximum amplitude is equal to or above the reference level, the circuit 24 generates a PWM signal having a pulse width T1. If the amplitude of the signal is below the preset reference level, the circuit 24 generates a PWM signal having a pulse width T2>T1. The PWM signal having the pulse width T1 will be referred to below as F (liquid), and the PWM signal having the pulse width T2 will be referred to as L (air) (FIG. 2).

In the present embodiment, there is only one reference level preset. It is, however, also possible for a plurality of reference levels to be preset to enable a distinction to be made between different attenuations of the signals.

The PWM signals are processed in the analyzing unit 21 block by block. Because, at T=50 ms, the cycle of the blood treating apparatus differs considerably from the temporal spacing of the measuring cycles (T=200 µs), the PWM signals are buffer stored in the buffer store 25 and are transferred block by block to the circuit 26 for signal analysis, in which the sequence of signals is acquired in an unbroken stream.

The signal analyzing circuit 26 is connected via a data line 27 to the control unit 15 of the dialysis apparatus, which control unit 15 is connected in turn via the control line 16 to the blood pump 13, In this way the analyzing circuit 26 receives the flow-rate of the blood flowing through the measurement gap, which is preset by the blood pump 13. The signal analyzing circuit 26 is also connected, via signal lines 28 and 29 to a first and a second signaling means 30 and 31, which are able to give an acoustic and/or visual alarm. A control line 32 runs from the signal analyzing circuit 26 to the control unit 15 for the transmission of a control signal. If this control signal is applied to the control unit 15, the control unit immediately suspends the treatment of the blood by actuating the venous tube clamp 33 to clamp off the blood takeaway line 7 and stop the blood pump 13.

Figure 3:
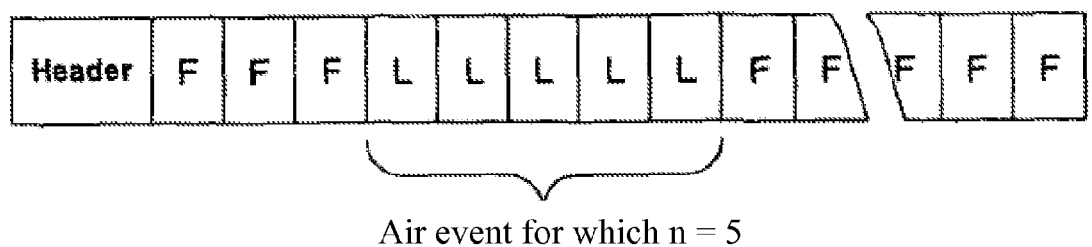
FIG. 3 shows the signal sequence of the pulse width modulated signals.

The way in which the signal analyzing circuit 26 operates will be explained in detail below. The circuit 26 has means 26A for determining the number of successive intervals of time in which the maximum amplitude of the signal is below the preset reference level, i.e. the PWM signal L is present in the given interval of time. The signal analyzing circuit thus determines the number of PWM signals L which occur in continuous succession. FIG. 3 shows an example of the signal sequence. In this example there are 5 PWM signals L (n=5) in direct succession to one another.

Figures 4, 5:
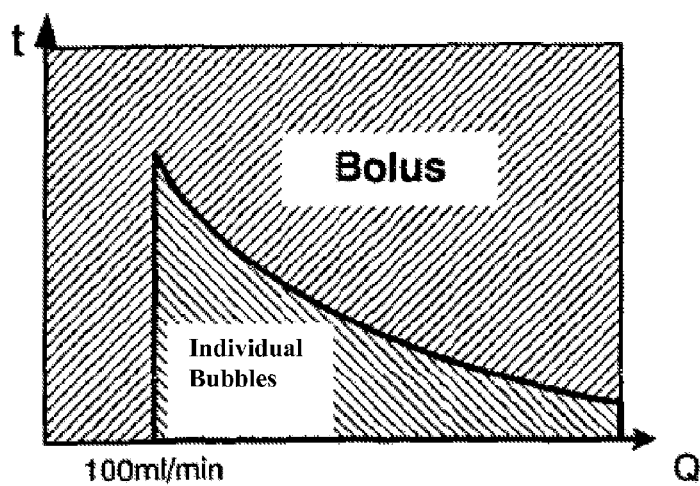
FIG. 4 is a table in which the limiting value for the number of successive intervals of time in which the level of the received ultrasonic signal is below the preset reference level is shown as a function of the flow-rate of the flowing liquid.
FIG. 5 shows the limiting value, which is laid down as a function of the flow-rate of the flowing liquid, as shown in the table in FIG. 4.

The signal analyzing circuit 26 also has means 26B by which a limiting value N is laid down for the successive PWM signals L as a function of the flow-rate of the blood. The individual limiting values for the individual flow-rates are determined empirically. FIG. 4 is a table in which the limiting values N for the successive PWM signals L are shown as a function of the flow-rate (BP rate) of the blood pump 13. The allocation of the values N to the individual flow-rates is stored in memory 26C of the signal analyzing circuit 26.

The signal analyzing circuit also has means 26D for comparing the number n of successive PWM signals L which are determined with the limiting value N laid down, which latter is taken from the memory 26C, and means 26E for detecting a first incident. The first incident is detected when the number of successive PWM signals L is above the limiting value N that has been laid down. When this is the case, the means 26E for detecting the first incident transmits an alarm signal to the first alarm unit 30, which generates an acoustic and/or visual alarm. The circuit 26 also generates a control signal for the control unit 15 of the dialysis apparatus, which at once suspends the treatment of the blood. This prevents the air that has been detected by the analyzing unit 21 from being infused into the patient.

In practice, it may happen that, due to disruptions or interference, individual PWM signals F or other signals may be found in a continuous sequence of PWM signals L. These spurious signals could severely falsify the signal analysis because it might be assumed that there was a break in the signal sequence when the spurious signals occurred. The signal analyzing circuit therefore also has one or more spurious-signal filters by which the occurrence of individual PWM signals F or other spurious signals in a fairly long sequence of PWM signals L is detected and the spurious signals eliminated. Known algorithms for error detection are used for this purpose.

In the event that the number n of successive PWM signals L is equal to or below the limiting value N laid down, it is determined that a fairly large amount of air (a bolus) is not contained in the blood, but rather only one or more small air bubbles (individual bubbles) are present in the blood. This event is not alone considered to be an incident. Rather, the patient is not placed at risk until the complete volume of air contained in the blood exceeds a preset reference value during the treatment of the blood.

The signal analyzing circuit 26 therefore has means 26F for determining the number of events p in which the number n of successive PWM signals L is equal to or below the limiting value N laid down. Also provided are means 26G for comparing the number p of such events with the preset reference value P, and means 26H for detecting a second incident. The second incident is detected when the number p of events is above the preset reference value P. A preset reference value P is, for example, between 8 and 12. If the second incident is detected, the means 26H for detecting the second incident transmits a second alarm signal to the second alarm means 31 and the alarm means 31 generate an acoustic and/or visual alarm that is different from the first alarm. In this case, a control signal is generated for the control unit of the dialysis apparatus to actuate the venous tube clamp 33 to clamp off the blood takeaway line 7 and to stop the blood pump 13.

The monitoring arrangement according to the invention allows various incidents to be detected reliably and a reliable distinction to be made between incidents to increase the safety of dialysis treatment.

The invention claimed is:

1. A method of monitoring a flowing medium for the presence of air, comprising:
 coupling of a sequence of ultrasonic signals of at least one preset amplitude into the flowing medium;
 receiving the ultrasonic signals emerging from the flowing medium over a time interval; for each ultrasonic signal:
  comparing the amplitude, or a parameter which correlates with amplitude, of the ultrasonic signal with a preset reference level;
  determining that a given volume of air is present in the flowing medium if the amplitude of the ultrasonic signal is below the preset reference level;
  determining that the given volume of air is not present in the flowing medium if the amplitude of the ultrasonic signal is equal to or above the preset reference level;
 determining the flow-rate of the flowing liquid and creating a limiting value (N) as a function of the flow-rate;
 determining a number of successive time intervals (n) in which the amplitude of the ultrasonic signal is below the preset reference level;
 comparing the number of successive time intervals (n) with the limiting value (N);
 concluding that there is a first incident if the number of successive time intervals (n) is above the limiting value (N), wherein the first incident is a large air bubble;
 determining a number of events (p) in which the number of successive time intervals (n) is equal to or below the limiting value (N);
 comparing the number of events (p) with a preset reference value (P);
 concluding that there is a second incident if the number of events (p) is above the preset reference value (P), wherein the second incident is a plurality of small air bubbles;
 generating a first alarm signal, a first control signal, or both a first alarm signal and a first control signal when the first incident is detected; and
 generating a second alarm signal, a second control signal, or both a second alarm signal and a second control signal, when the second incident is detected.

2. The method of claim 1, further comprising:
 generating a first signal if the amplitude of the ultrasonic signal received is below the preset reference level;
 generating a second signal if the amplitude of the ultrasonic signal received is equal to or above the preset reference level; and
 storing the two signals at a temporal spacing.

3. The method according to claim 2, wherein the first and second signals are combined into signal blocks and the signal blocks are buffer stored before the analysis.

4. The method of claim 1, further comprising:
 generating a first pulse width modulated signal (F) having a first pulse width ($T_1$) if the amplitude of the ultrasonic signal is equal to or above the preset reference level; and
 generating a second pulse width modulated signal (L) having a second pulse width ($T_2$) if the amplitude of the ultrasonic signal is below the preset reference level.

5. The method of claim 1 wherein the flowing medium is blood in an extra-corporeal blood circulatory system.

6. A system for monitoring a flowing medium for the presence of air, comprising:
 an ultrasonic emitter for coupling an ultrasonic signal of at least one preset amplitude into the flowing medium;
 an ultrasonic receiver for receiving the ultrasonic signal emerging from the flowing liquid;
 an analyzing unit comprising:
  means for comparing the amplitude, or a parameter which correlates with amplitude, of each of the ultrasonic signals which are received in a continuous sequence of intervals of time with a preset reference level, it being concluded that a given volume of air is present in the flowing liquid during the given interval of time if the amplitude of the ultrasonic signal is below the preset reference level and it being concluded that the given volume of air is not present if the amplitude of the ultrasonic signal is equal to or above the preset reference level;
  means for determining a number of successive intervals of time (n) in which the amplitude of the ultrasonic signal received is below the preset reference level;
  means for determining the flow-rate of the flowing liquid and for laying down a limiting value (N) as a function of the flow-rate;
  means for comparing the number of successive intervals of time (n) with the limiting value (N); and
  means for detecting a first incident when the number of successive intervals of time (n) is above the limiting value (N), wherein the first incident is a large air bubble;
  means for determining a number of events (p) in which the number of successive intervals of time (n) is equal to or below the limiting value (N);
  means for comparing the number of events (p) with a preset reference value (P); and
  means for detecting a second incident when the number of events (p) is above the preset reference value (P), wherein the second incident is a plurality of small air bubbles; and
 a means for generating a first alarm signal, a first control signal, or both a first alarm signal and a first control signal when the first incident is detected; and
 a means for generating a second alarm signal, a second control signal, or both a second alarm signal and a second control signal, when the second incident is detected.

7. The system of claim 6, wherein the analyzing unit further comprises:
 means for generating a first signal if the amplitude of the ultrasonic signal received is below the preset reference level;

means for generating a second signal if the amplitude of the ultrasonic signal received is equal to or above the preset reference level; and means for storing the two signals at a temporal spacing.

8. The system of claim 6 wherein the analyzing unit further comprises:

means for generating a first PWM signal (F) having a first pulse width ($T_1$) if the amplitude of the ultrasonic signal is equal to or above the preset reference level; and means for generating a second PWM signal (L) having a second pulse width ($T_2$) if the amplitude of the ultrasonic signal is below the preset reference level.

9. The system of claim 6 wherein the analyzing unit is so arranged that the first and second signals are combined into signal blocks and the analyzing unit further comprises a buffer store in which the signal blocks are buffer stored before the analysis.

* * * * *